US006617141B1

(12) United States Patent
Kaimal et al.

(10) Patent No.: US 6,617,141 B1
(45) Date of Patent: Sep. 9, 2003

(54) ENZYMATIC PROCESS FOR PREPARING REDUCED-CALORIE FATS CONTAINING BEHENIC ACID

(75) Inventors: Thengumpillil N. B. Kaimal, Andhra Pradesh (IN); Sanjit Kanjilal, Andhra Pradesh (IN); Raghapudi B. N. Prasad, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/207,056

(22) Filed: Dec. 8, 1998

(30) Foreign Application Priority Data

Dec. 8, 1997 (IN) ........................................ 3504/DEL/97

(51) Int. Cl.[7] ................................................. C12P 7/64
(52) U.S. Cl. ........................ 435/134; 435/135; 426/601
(58) Field of Search ................................ 435/134, 135; 426/601

(56) References Cited

U.S. PATENT DOCUMENTS 4,877,636 A * 10/1989 Koyano ....................... 426/607
5,529,803 A *  6/1996 Yamada ....................... 426/606

FOREIGN PATENT DOCUMENTS

WO            96/10643         *   4/1996

OTHER PUBLICATIONS

Peters et al., J. Am. Coll. Toxicol., vol. 10, p. 357–67, 1991.*
Yoon, et al., Biosci., Biotechnol., Biochem. (1998), 62(1), 170–172.*

* cited by examiner

*Primary Examiner*—Irene Marx
(74) *Attorney, Agent, or Firm*—Pennie & Edmonds LLP (57) ABSTRACT

The invention for a process for the preparation of reduced caloric fat, which comprises esterification of edible oils with a source of behenic acid in the presence of a catalyst, at a temperature in range of 25° C. to 150° C., at least for 0.5 hr and then recovering and purifying the reduced calorie fat using conventional methods.

13 Claims, 2 Drawing Sheets

Graphical representation of mean body weight gain of all the test groups including the adlibitum group in the restricted diet growth experiment. (Table 1A)

Fig. 1A. Graphical representation of mean body weight gain of all the test groups including the adlibitum group in the restricted diet growth experiment. (Table 1A)

Fig. 1B. Graphical representation of the growth pattern of the 10% SO (Control group) and 10% SL3 (Experimental group) in the adlibitum experiment. (Table 2B)

ENZYMATIC PROCESS FOR PREPARING REDUCED-CALORIE FATS CONTAINING BEHENIC ACID

CROSS-REFERENCE TO RELATED APPLICATIONS

This application claims priority to Indian Application No. 3504/DEL/97, filed Dec. 8, 1997.

1. Field of the Invention

This invention relates to a process for the preparation of reduced calorie fats. This invention particularly relates to the preparation of reduced calorie fats by incorporating behenic acid into edible oils such as sunflower, groundnut, safflower, rapeseed, soybean and fish oils. More particularly, it provides a reduced calorie plastic for containing essential fatty acids and natural antioxidants using different processes involving chemical interesterification of 1,3-dibehenin and edible oils or chemical interesterification of 1,3-dibehenin based structured fat and edible oils or enzymic transesterification of edible oils with alkyl behenates.

2. Background

Typical fats and oils provide approximately 6 kcal/g of metabolizable energy compared to 4 kcal/g for protein or carbohydrate [Atwater, W. O. et al., Annu. Rep. Storrs Agric. Exp. Stn. (1903) No.15, 123–146 & Maynard, L. A., J. Nutr. 28 (1944) 443–453]. In addition to the caloric and nutritional value, fats have many functions in the diet. Fats and oils carry, enhance and release the flavours of other food components, delays digestion, increases palatability of food and imparts the feeling of satiety. Certain unsaturated fatty acids like 9,12-octadecenoic acid (linole acid) which are known to be essential fatty acids are necessary as they are not produced in the body. Fats and oils are also associated with the fat-soluble vitamins A, D, E and K, and the absorption of these vitamins is impaired at very low fat intakes. Fat is also associated with diseases such as coronary heart disease and cancer, a high fat diet being positively linked to both. The U.S. Surgeon General has recommended that no more then 30% of the dietary calories should be derived from fat [U.S. Department of Health and Human Services, The Surgeon General's Report on Nutrition and Health, DHHS (PHS) Publication 88-50210, [U.S.GPO., Washington, D.C. (1988)]. Regulatory and advisory bodies advocate a lowered fat intake in order to reduce the incidence and morbidity of many coronary diseases, stroke, high blood pressure, obesity and diabetes.

However, food habits are difficult to change and the positive contribution of fats to increase the palatability of foods is generally recognized. The level of fat in the diet of affluent societies is too high and needs to be lowered. Reduced fat or low calorie foods as well as fat replacers or substitutes have been the result of numerous attempts to meet the health recommendations without changing traditional ways of eating.

Three different types of fat replacers namely carbohydrate-based, protein-based and fat-based are reported in the literature.

Carbohydrate-based fat replacers consists of many products like dextrin, polydextrose, maltodextrin, cellulose, gums etc., which are used as thickeners and stabilizers in frozen desserts, salad dressings, margarine type spreads, baked products, frostings and snacks. Many products based on starch have been developed specifically as fat mimetic [Alexander, R. J., Cereal Food World 40 (1995) 366–368].

However, starch based products are not good for diabetics for whom good glucose control is necessary [Grundy, S. M., Diabetics Care 14 (1991) 796–801]. The U.S. Food and Drug Administration (FDA) regulations state that sensitive individuals may experience a laxative effect from excessive consumption of maltrodextrins [U.S.A. Food & Drug Administration Regulations 21 CFR Part 105]. Some popular examples of carbohydrate based fat replacers are Stellar, Remyrise AP, N-Oil, Lycadex, Maltrin, Ex-cel, Fibercel, Centu Tex, Fibrex etc. [Jones, J. M., Chemistry & Industry, (1996) 494–498].

Protein-based fat replacers are produced using common proteins such as egg white, skimmed milk or whey by microparticulating them into a particle size of 1–3 µm to obtain a slippery and creamy fat like feeling which provide 1–2 kcal/g [Singer, N. S., et al., J.] Amer. Coll. Nutr. 9 (1990) 388–397]. These products are being used in variety of food products such as yogurts, cheese products, frozen desserts and also for formulating low fat baked goods such as cheese cakes and pie crust. Gelatin from fish waste was also reported as a fat replacer to use as a viscosity modifier and to impart a creamy texture. However, such fat replacers are reported to be hypersensitive for persons with allergy to the base proteins [Young, V. R., et al., J. Amer. Coll. Nutr. 9 (1990) 418–426]. Some examples of protein based fat replacers popular in the market are Dairylight, Simplesse, Lita, Calpra 75 etc. [Jones, J. M., Chemistry & Industry (1996) 494–498].

Carbohydrate-based and protein-based fat replacers are presently used in a range of foods, and are effective in delivering fat-like texture where the final product has a significant water content and is not exposed to extremely high temperatures or temperature variations [Mela, D. J., Fett/Lipid 98 (1996) 50–55]. These problems can be overcome by fat-based low calorie fats.

Fat-based low calorie fats have many advantages like functional and sensory properties very similar to the normal fats when compared to the carbohydrate and protein-based fat replacers. They also provide both the characteristic texture and flavour effects of native fats.

Many fat-based low calorie fats are reported in the literature namely propoxylated glycerols esterified with fatty acid chlorides [Masten, L. W., EP 571,219 (1993); White, J. F. et al., EP 325,010 (1989)]; fatty acid diesters of $C_{4-10}$ dihydric alcohols [Klemann, L. P. et al., U.S. Pat. No. 5,286,512 (1994); Klemann, L. P. et al., U.S. Pat. No. 5,006,351 (1991)]; trioltriester derivatives [Klemann, L. P. et al., U.S. Pat. No. 5,043,179 (1991)]; polyol fatty acid polyesters [Kester, J. J. et al., U.S. Pat. No. 5,314,707 (1994); Letton, J. C., et al., 5,306,514 (1994)]; polyvinyloleate [D'Amelia, R. P. et al., U.S. Pat. No. 4,915,974 (1990)]; oleoylloeate [Jacklin, P. T. et al., U.S. Pat. No. 4,915,974 (1990)]; bis-oleoylaspartyladipare [Klemann, L. P. et al., U.S. Pat. No. 5,139,807 (1992)]; esterified alkoxylated mono- and diglycerides [Cooper, C. F. et al., U.S. Pat. No. 5,371,253 (1994)]; triglycerides containing $C_{12-22}$ fatty acids having alkyl groups at least at the position 5,9,13 of the alkyl chain [Tagiri, M. et al., JP 04,325,055 (1992)]; 1,3-didecanoylglycerol [Mazur, A. W. et al., U.S. Pat. No. 5,137,660 (1992)]; alkyl or polyol thioesters [Klemann, L. P., U.S. Pat. No. 4,992,293 (1991)]; propyleneglycol diesters of medium chain and long chain saturated fatty acids [Stipp, G. K. et al., EP 495,553 (1992)]; alkylmalonic acid diesters [Fulcher, J. G. et al., Aus. Pat. No. 594,040 (1990)]; esterified polyoxyalkylene block co-polymers [Cooper, C. F. et al., EP 481,717 (1992)]; alkylglycoside fatty acid polyesters [Winter, D. D. et al., U.S. Pat. No. 4,942,054 (1990)]; fatty acid esters of sucrose [Letton, J. A., et al., EP 375,027 (1990)]; sorbitol fatty acid esters [Gruetzmacher, G. D., EP, 591,258 (1994)]; partially esterified polysaccharide with fatty acids [White, J. F. U.S. Pat. No. 4,959,466 (1990)]; alkoxylated sugar and sugar alcohol esters [Ennis, J. L. et al., EP 425,635 (1991)]; polysaccharide fatty acid polyester [Meyer, R. S. et al., U.S. Pat. No. 4,973,489 (1990)]. All these are unnatural compounds not normally encountered in human diet and the long term affects of consumption of such are presently unknown.

Examples of the more commonly known low calorie fats are OLESTRA™, medium chain triglycerides (MCTs), Caprenin and SALATRIM™. OLESTRA™ is a mixture of hexa-, hepta-, and octa- fatty acid esters of sucrose. The physical properties of sucrose polyesters are similar to normal triglycerides [Jandacek, R. J., et al., Chem, Phys. Lipids 22 (1978) 163–176]. OLESTRA™ is adaptable to most application where fats and oils are used. However, the major drawback to OLESTRA™ is "anal leakage", the result of a non-digestible fat passing through the digestive system. OLESTRA™ also blocks the absorption of fat soluble vitamins [Bailey's Industrial Oil & fat Products, Vol. 1, Ed. Y. H. Hui (1996), p. 286; Jones D. Y. et al., Amer. J. Clin. Nutr. 53 (1991) 1282–1287 and Dasher, G., et al., FASEB J. 8 (1994) 443].

MCTs are triglycerols composed of $C_6$, $C_8$ and $C_{10}$ saturated fatty acids. Hunder, J. E., et al., [U.S. Pat. No. 4,863,753 (1989)] reported a low calorie peanut butter containing $\geq 10\%$ MCTs. A peanut butter composition containing MCTs (41.96%) was reported to have excellent consistency and contained at least 10% fewer calories than the normal fat. However, MCTs may be toxic and may induce metabolic acidosis in large doses [Akoh, C. C. Inform 6 (1995) 1055–1061].

SALATRIM™ (short and long acylglycerol molecules) is a family of structured triacylglycerols prepared by interesterifying a completely hydrogenated vegetable oil with triacetin, tripropionin and/or tributyrin using sodium methoxide as a catalyst at 100–150° C. [Wheeler, E. L. et al., U.S. Pat. No. 5,258,197 (1991); Klemann, L. P. et al., 42, J. Agr. Food Chem. (1994) 42, 442–446]. Thus, the SALATRIM™ triglycerides are composed of mixtures of long-chain saturated fatty acids (predominantly stearic) and short-chain fatty acids (acetic propionic, and/or butyric) esterified to the glycerol backbone. A similar low calorie fat namely acetyl distearoyl glyceride was prepared by Wheeler, E. L. et al. [U.S. Pat. No. 5,258,197 (1991)]. Extensive testing in animals of SALATRIM™ has shown no changes in the intestinal microflora or secondary bile acids, and no increased mutagenicity or other toxicological effects [Hayes, J. R., el al., J. Agr. Food Chem. 42 (1994) 500–514; Scheinbach, S., et al., ibid, 42 (1994) 572–580; Hayes, J. R., et al., ibid, 42 (1994) 539–551; Hayes, J. R., et al., ibid, 42 (1994) 515–520; and Hayes, J. R., et al., ibid, 42 (1994) 521–527]. However, SALATRIM™ contains unnatural components such as very low molecular weight fatty acids and does not contain essential fatty acids.

Caprenin, a structured triglyceride consisting of caprylic and capric acids and the very long chain behenic acid which was developed for use in chocolate preparation. It yields only 5 cal/g instead of 9 cal/g because the short chain fatty acids have lower energy values and behenic acid is not well absorbed [Peters, J. C. et al., J. Am. Coll. Toxicol. 10 (1991) 357–67; Webb, D. R., et al., ibid 10 (1991) 341–356; Webb, D. R. et al, ibid., 10 (1991) 325–340]. Glycerin was esterified first with behenic acid to form glycerylmonobehenate, which was then reacted with capric and caprylic acids or their anhydrides, and then purified by molecular distillation and steam deodorization. Yoshida, T. et al., [JP 0559392 (1991)] reported the synthesis of 2-behenyl-1,3-dicaproyl glycerol by reacting tribehenin and ethyl caproate in the presence of lipase and the product's feed study on rats showed that absorption of the structured triglycerides was significantly lower and its excretion into feces was higher than other oils. In another report Yoshida R., et al., [Shoka to Kyushu 14 (1991) 27–30 C. A. 117: 47249 (1992)] reported the synthesis of triglycerides with a randomly placed long chain fatty acid (behenic acid) and two medium chain fatty acids (capric and caproic acids) and included it in the diet of rats. These triglycerides were poorly absorbed from the intestine; absorption of behenic acid was particularly poor. Caprenin feeding studies have shown that it produces no toxic effects when fed as the primary source of dietary fat [Webb, D. R. et al., Food Chem. Toxicol. 31 (1993) 935–946]; Webb, D. R., et al., J. Amer. Coll. Toxicol. 10 (1991) 341–356 and Webb, D. R., et al, ibid, 10 (1991) 325–340]. However, a six week study of relative effects on serum lipids and apolipoproteins of a caprenin rich diet feeding studies by Wardlaw, G. M., et al., [Am. J. Clin. Nutr. 61 (1995) 535–542] showed that caprenin can contribute to hypercholesterolemia in men and gastrointestinal complaints in some individuals.

BRIEF DESCRIPTION OF THE DRAWINGS

FIG. 2B is a graphical representation of the growth pattern of the 10% SO (control group) and 10% SL 3 (experimental group) in the ad libitum experiment.

DETAILED DESCRIPTION

The low calorie fats reported so far does not contain essential fatty acids and the natural antioxidants normally found in natural oils and fats. Hence, the objective of the present invention is to provide reduced-calorie fats which fulfils the three basic functions of fat in foods: (1) a source of essential fatty acids, (2) a carrier for fat soluble vitamins, and (3) a source of energy for storage or oxidation. This is achieved by incorporating poorly absorbable behenic acid into edible oils particularly vegetable oils such as sunflower, safflower and groundnut oils. A further objective of the present invention was to provide a reduced calorie plastic fat of the consistency of vanaspati and which does not contain the deleterious trans fatty acids.

In the present invention, reduced-calorie fats were prepared by incorporating behenic acid into edible oils using three different routes.

In the first two methods for the preparation of reduced-calorie plastic fats, 1,3-dibehenin prepared from mustard oil was used as a source of behenic acid. Other cruciferae oils such as rapeseed oil could also be used for this preparation. Mustard oil consists of about 44% of erucic acid along with other normal fatty acids. 1,3-Dierucin is prepared from mustard oil using the methodology developed by us previously [Kaimal T. N. B., et al. Biotechnology Letters 15, (1993) 353–356)] by lipase (from Candida cylindracea) hydrolysis under restricted water conditions and isolated 1,3-dierucin from the reaction mixture by crystallization from acetone at 10° C. 1,3-Dierucin is hydrogenated to 1,3-dibehenin using conventional method with 10% palladium-carbon as catalyst under pressure (2–3 kg/cm$^2$) in chloroform. After removal of the catalyst by filtration, 1,3-dibehenin is recrystallized from acetone.

The first route comprises interesterification of vegetable oils, exemplified by sunflower oil, and 1,3-dibehenin using sodium methoxide as catalyst at a concentration in the range of 0.3% to 0.5% by weight of the substrate at a temperature in the range of 80–150° C. for a period in the range of 0.5 to 1.0 hour, purifying the product by silicic acid column chromatography to yield a reduced-calorie fat. The product thus prepared from sunflower oil and dibehenin in the molar ratio of 1:0.5 contained 29.8% of behenic acid and 44.6% of linoleic acid while a product containing 52.5% of behenic acid and 24.8% linoleic acid was obtained when the molar ratios were 1:1.

The second route provides a process for the preparation of reduced-calorie fat which comprises incorporation of sunflower oil fatty acids into the second position of 1,3-dibehenin to prepare a structured fat followed by its chemical interesterification with vegetable oils exemplified by sunflower oil. Accordingly this route consists of the following steps: a) saponification of sunflower oil to obtain fatty acid mixture, b) conversion of fatty acid mixture to anhydrides c) esterification of 1,3-dibehenin with the said fatty acid anhydrides to obtain structured fat, d) chemical interesterification of the structured fat with vegetable oils exemplified by sunflower oil, and e) isolation of reduced-calorie fat by silicic acid column chromatography.

Sunflower oil is saponified using conventional method by refluxing with 10% potassium hydroxide in ethanol and the saponified mass was neutralised with dilute hydrochloric acid and extracted with diethylether to obtain sunflower oil fatty acids. The sunflower oil fatty acid mixture was converted to their anhydride by treating with dicyclohexylcarbodiimide following conventional procedures. The fatty anhydride was then refluxed in chloroform with 1,3-dibehenin in presence of N,N-dimethylamino pyridine to obtain structured fat. The structured fat with a melting point of 55° C. was then interesterified with vegetable oils exemplified with sunflower oil using sodium methoxide as catalyst at a concentration in the range of 0.3% to 0.5% by weight of the substrate and at a temperature in the range of 80–150° C. for a period in the range of 0.5 to 1 hr till the randomization of the fatty acids was complete. The reduced-calorie fat was then purified by silicic acid column chromatography and found to contain about 32.1% of behenic acid and 33.7% of linoleic acid with a melting point of 36° C.

The third route of the present invention provides a process for the preparation of reduced-calorie fat which comprises transesterification of vegetable oils and alkyl behenate with lipase [from *Mucor miehei* (Lypozyme 1M 20), 30 BIU/g, supplied by Novo Industri A/S, Denmark] and purifying the structured fat by silicic acid column chromatography to yield a reduced-calorie structured fat containing 5 to 41% of behenic acid and 33 to 60% of linoleic acid which is,an essential fatty acid. Only a slight excess of alkyl behenate (1.2 mole equivalents to that of vegetable oil) is used for transesterification. The interesterified reduced-calorie fat containing about 33% of behenic acid was found to have a slip melting point of about 37° C. Various alkyl esters of behenic acid tried such as methyl, ethyl, isopropyl and n-butyl were used for this reaction but satisfactory levels of incorporation of behenic acid was obtained only when the ethyl esters were used.

The transesterification of sunflower oil and ethyl behenate is standardised by varying the enzyme concentration in the range of 1 to 4% by weight of the substrate, temperature in the range of 55–70° C. and reaction period in the range of 1–6 hrs. Of the various parameters studied, enzyme concentration of 2%, temperature of 60° C. and reaction period of 3 hr yielded a structured fat containing about 34% of behenic acid by GC analysis, and having a slip melting point of 37° C.

Accordingly the present invention provides a process for the preparation of reduced-calorie fat which comprises esterification of edible oils with a source of behenic acid such as herein described, in presence of a catalyst at a temperature in the range 25° C. to 150° C. at least for 0.5 hr. and then recovering and purifying the reduced-calorie fats using conventional methods such as herein described. Edible oils which may be used are such as sunflower, groundnut, safflower, soybean, rapeseed, fish oil etc. The sources of behenic acid which may be used are 1,3-dibehenin, alkyl behenate and a structured fat containing behenic acid described herein. The esterification temperature may be in the range of 25° C. to 150° C. depending on the type of catalyst used which may be an alkali metal alkoxide or a thermostable lipase enzyme such as Lipozyme. The esterification reaction may be effected in the time range of 0.5 hr to 6 hr. Recovery of the reduced-calorie fat may be effected by filtration followed by column chromatographic purification in case of enzymatic transesterification or by washing-off the catalyst alkali metal alkoxide in case of chemical transesterification.

The following examples illustrate the invention and should not be construed as the limit of the invention and the manner in which it is carried out.

EXAMPLES

Example 1 a) Preparation of 1,3-dibehenin

Mustard oil (100 gm) was mixed with tert-butanol (50 ml) and lipase from *Candida cylindracea* (700 mg) was added in small portions while stirring continuously. After the enzyme was dispersed uniformly, water was added intermittently at a rate of 3 ml/hr by a peristaltic pump for 2 h and stirred afterwards for an additional 12 hours. The mixture was centrifuged to separate the lipase. The reaction product had an acid value of 55.0. The solvent was removed under vacuum and the product dissolved in 300 ml of acetone and crystallized at 10° C. to yield dierucin (29 gm; colorless powder, m. pt. 45° C.). 1,3-dierucin was then hydrogenated using 10% Pd-C (1.5 gm) in chloroform (100 ml) at 2 $kg/cm^2$ hydrogen pressure for 4 hours. Catalyst was filtered off and 1,3-dibehenin was crystallized by adding acetone (50 ml) and then cooling at 0° C. Crystallized 1,3-dibehenin (24 gm; white flakes; m. pt. 88° C.) shows 92% behenic acid by Gas Chromatographic (GC) analysis.

b) Interesterification of Dibehenin and Sunflower Oil

Sunflower oil (1 g) was mixed with 1,3-dibehenin (0.421 g) and kept under vacuum at 110° C. for 30 minutes. Then sodium methoxide in methanol (0.5% w/w; 45 μl) was added and stirred for 1 hour under vacuum. The product was taken in 20 ml of diethylether and washed with water to remove sodium methoxide. The reduced calorie fat containing behenic acid was purified by silicic acid column chromatography using hexane:ethyl acetate (95:5, v/v) as eluant and found to contain behenic acid, 29.8%; oleic acid, 16.7%; linoleic acid, 44.6% and others, 8.9%. The product had slip melting point of 34° C.

Example 2

Sunflower oil (1 g) was mixed with 110° C. 1,3-dibehenin (0.842 g) in a two-necked 25 ml of R.B. flask and kept under vacuum at 110° C. for 30 minutes. Then sodium methoxide in methanol (0.5% w/w; 55 μl.) was added and stirred for 1 hour under vacuum. The product was taken in 20 ml of diethylether and washed with water to remove sodium methoxide. The reduced calorie fat containing behenic acid was purified by silicic acid column chromatography using hexane:ethyl acetate (95:5, v/v) as eluant and found to contain behenic acid, 52.5%; oleic acid, 13.1%; linoleic acid, 24.8% and others, 9.6%. The yield of the reduced-calorie fat was 1.0 g and its slip melting point was found to be 50° C.

Example 3

Sunflower oil(5 g) was saponified by refluxing with 10% potassium hydroxide in ethanol (20 ml) for one hour. The saponified mass was neutralised with dil. hydrochloric acid and extracted with diethylether to obtain sunflower oil fatty acids (4.5 g). The fatty acid mixture (4.5 g) was converted to anhydride by treating it with dicyclohexylcarbodiimide (4.24 g) in carbon tetrachloride (30 ml) for overnight. The precipitated dicyclohexyl urea was filtered out and filtrate was concentrated to obtain fatty acid anhydride (4.1 g). The anhydride (4.1 g) was then refluxed with 1,3-dibehenin (5 g) in 50 ml chloroform for 10 hours in presence of N,N-dimethylaminopyridine (1.2 g). The resulting structured fat having behenic acid in 1,3position and sunflower oil fatty acids in 2 position was purified by silicic acid column chromatography by eluting with hexane:ethyl acetate (95:5; v/v). An yield of 6 g of structured fat (melting point 55° C.) was obtained with fatty acid composition of behenic, 72.2%; oleic, 8.1%; linoleic, 12.5%; others 7.2% by GC analysis. This was further interesterified with sunflower oil. Sunflower oil (5.2 g) was mixed with the structured fat (6 g) and kept the contents under vacuum at 110° C. for 30 min. Sodium methoxide (0.5% w/w; 0.35 ml) was added and the mixture stirred for one hour under vacuum. The product was taken in diethyl ether (150 ml) and washed with water to remove the excess sodium methoxide. The resulting reduced-calorie fat (10 g) was found to contain behenic acid, 32.1%; oleic acid, 22.1%, linoleic acid, 33.7% and others, 12.5% with a slip melting point of 36° C.

Example 4

Sunflower oil (2.5 g) and 1.22 g of ethyl behenate were taken in a screw-capped test tube and the mixture was homogenized by agitation for 15 min. at 60° C. About 75 mg (2% by wt. of the substrate) of Lipozyme 1M 20 was added followed by agitation of the mixture for 6 hr at 60° C. After the reaction, the enzyme was filtered out and the enzyme was washed with hexane for its re-use. The product was purified by silicic acid (60–120 mesh) column chromatography. The ethyl esters were eluted by using hexane:ethyl acetate (99:1, v/v) followed by triglycerides using a solvent mixture of hexane:ethyl acetate (95:5, v/v). The triglycerides were found to contain 36% of behenic acid along with oleic (15.6%), linoleic (37.7%) and other fatty acids (10.5%) with a slip melting point of 40° C.

Example 5

Sunflower oil (2.5 g) and 1.22 g of ethyl behenate were taken in a screw-capped test tube and the mixture was homogenized by agitation for 15 min. at 60° C. About 75 mg (2% by wt. of the substrate) of Lipozyme 1M 20 was added followed by agitation of the mixture for 3 hr at 60° C. After the reaction, the enzyme was filtered out and the enzyme was washed with hexane for its re-use. The product was purified by silicic acid (60–120 mesh) column chromatography. The ethyl esters were eluted by using hexane:ethyl acetate (99:1 v/v) followed by triglycerides using a solvent mixture of hexane:ethyl acetate (95:5, v/v). The triglycerides were found to contain 34.7% of behenic acid along with oleic (17.1%), linoleic (35.2%) and other fatty acids (13.0%) with a slip melting point of 37° C.

Example 6

Sunflower oil (2.5 g) and 1.15 g of methyl behenate were taken in a screw-capped test tube and the mixture was homogenized by agitation for 15 min. at 60° C. About 73 mg (2% by wt. of the substrate) of Lipozyme 1M 20 was added followed by agitation of the mixture for 3 hr at 60° C. After the reaction, the enzyme was filtered out and the enzyme was washed with hexane for its re-use. The product was purified by silicic acid (60–120 mesh) column chromatography. The methyl esters were eluted by using hexane:ethyl acetate (99:1, v/v) followed by triglycerides using a solvent mixture of hexane:ethyl acetate (95:5, v/v). The triglycerides were found to contain 16.5% of behenic acid along with oleic (23%), linoleic (47.9%) and other fatty acids (12.6%) with a slip melting point of 20° C.

Example 7

Sunflower oil (2.5 g) and 1.28 g of isopropyl behenate were taken in a screw-capped test tube and the mixture was homogenized by agitation for 15 min. at 60° C. About 76 mg (2% by wt. of the substrate) of Lipozyme 1M 20 was added followed by agitation of the mixture for 3 hr at 60° C. After the reaction, the enzyme was filtered out and the enzyme was washed with hexane for its re-use. The product was purified by silicic acid (60–120 mesh) column chromatography. The isopropyl esters were eluted by using hexane:ethyl acetate (99:1, v/v) followed by triglycerides using a solvent mixture of hexane:ethyl acerate (95:5, v/v). The triglycerides were found to contain 5.1% of behenic acid along with oleic (26.5%), linoleic (60.0%) and other fatty acids (8.4%) with a slip melting point of <15° C.

Example 8

Sunflower oil (2.5 g) and 1.31 g of n-butyl behenate were taken in a screw-capped test tube and the mixture was homogenized by agitation for 15 min. at 60° C. About 76 mg (2% by wt. of the substrate) of Lipozyme 1M 20 was added followed by agitation of the mixture for 3 hr at 60° C. After the reaction, the enzyme was filtered out and the enzyme was washed with hexane for its re-use. The product was purified by silicic acid (60–120 mesh) column chromatography. The n-butyl esters were eluted by using hexane:ethyl acetate (99:1, v/v) followed by triglycerides using a solvent mixture of hexane:ethyl acetate (95:5, v/v). The triglycerides were found to contain 14.2% of behenic acid along with oleic (23%), linoleic (52.3%) and other fatty acids (10.5%) with a slip melting point of 18° C.

Example 9

Sunflower oil (2.5 g) and 1.22 g of ethyl behenate were taken in a screw-capped test tube and the mixture was homogenized by agitation for 15 min. at 70° C. About 75 mg (2% by wt. of the substrate) of Lipozyme 1M 20 was added followed by agitation of the mixture for 3 hr at 70° C. After the reaction, the enzyme was filtered out and the enzyme was washed with hexane for its re-use. The product was purified by silicic acid (60–120 mesh) column chromatography. The ethyl esters were eluted by using hexane:ethyl acetate (99:1, v/v) followed by triglycerides using a solvent mixture of hexane:ethyl acetate (95:5, v/v). The triglycerides were found to contain 19.3% of behenic acid along with oleic (20.5%), linoleic (48.5%) and other fatty acids (11.7%) with a slip melting point of 22° C.

Example 10

Sunflower oil (2.5 g) and 1.22 g of ethyl behenate were taken in a screw-capped test tube and the mixture was homogenized by agitation for 15 min. at 70° C. About 75 mg (2% by wt. of the substrate) of Lipozyme 1M 20 was added followed by agitation of the mixture for 3 hr at 55° C. After the reaction, the enzyme was filtered out and the enzyme was washed with hexane for its re-use. The product was purified by silicic acid (60–120 mesh) column chromatography. The ethyl esters were eluted by using hexane:ethyl acetate (99:1, v/v) followed by triglycerides using a solvent mixture of hexane:ethyl acetate (95:5, v/v). The triglycerides were found to contain 19.3% of behenic acid along with oleic (21.5%), lirioleic (51.9%) and other fatty acids (11.7%) with a slip melting point of 20° C.

Example 11

Safflower oil (2.5 g) and 1.22 g of ethyl behenate were taken in a screw-capped test tube and the mixture was homogenized by agitation for 15 min. at 60° C. About 75 mg (2% by wt. of the substrate) of Lipozyme 1M 20 was added followed by agitation of the mixture for 3 hrs at 60° C. After the reaction, the enzyme was filtered out and the enzyme was washed with hexane for its re-use. The product was purified by silicic acid (60–120 mesh) coluitun chromatography. The ethyl esters were eluted by using hexane:ethyl acetate (99:1, v/v) followed by triglycerides using a solvent mixture of hexane:ethyl acetate (95:5, v/v). The triglycerides were found to contain 24.7% of behenic acid along with oleic (12.4%), linoleic (51.5%) and other fatty acids (11.4%) with a slip melting point of 28° C.

Example 12

Groundnut oil (2.5 g) and 1.22 g of ethyl behenate were taken in a screw-capped test tube and the mixture was homogenized by agitation for 15 min. at 60° C. About 75 mg (2% by wt. of the substrate) of Lypozyme 1M 20 was added followed by agitation of the mixture for 3 hr at 60° C. After the reaction, the enzyme was filtered out and the enzyme was washed with hexane for its re-use. The product was purified by silicic acid (60–120 mesh) column chromatography. The ethyl esters were eluted by using hexane:ethyl acetate (99:1, v/v) followed by triglycerides using a solvent mixture of hexane:ethyl acetate (95:5, v/v). The triglycerides were found to contain 22.0% of behenic acid along with oleic (39.5%), linoleic (19.7%) and other fatty acids (18.8%) with a slip melting point of 25° C.

One embodiment of the invention relates to providing a low calorie fat composition comprising:

| Fatty Acid | W % |
|---|---|
| Palmitic | 4.9 |
| Stearic | 4.8 |
| Oleic | 17.1 |
| Linoleic | 35.2 |
| Arachidic | 1.7 |
| Behenic | 34.7 |
| Lignoceric | 1.6 |

Preferably, the fat composition comprising the following solid Fat index:

| Temperature (° C.) | SFI |
|---|---|
| 15 | 11.5 |
| 20 | 9.9 |
| 25 | 9.4 |
| 30 | 8.2 |
| 35 | 3.4 |
| 40 | 0.0 |

Typically, the physical properties of the composition are:

| Physical Properties | |
|---|---|
| Saponification value | 179.8 |
| Iodine value | 75.9 |
| Acid value | <0.1 |
| M.Pt. (° C.) | 37.0 |

In another embodiment, the fatty acid composition comprising the following triglycerides:

| Triglyceride composition (by HPLC) | | |
|---|---|---|
| ECN* | Expected TAG** | Wt % |
| C42 | LLL | 12.1 |
| C44 | LLO | 10.8 |
| C44 | LLP | 2.8 |
| C46 | SLL; POL | 3 |
| C46 | LOO | 2.4 |
| C48 | SOL; OOO | 2.6 |
| C50 | BLL | 32.3 |
| C52 | BLO | 12.2 |
| C52 | BLP | 2.4 |
| C54 | BOO | 1.9 |
| C54 | BOP | 2.1 |
| C56 | BOS | 1.7 |
| C58 | BLB | 11.4 |
| C60 | BOB | 2.1 |

*ECN = Effective carbon number
**B: behenic acid
P: palmitic acid
L: linoleic acid
O: oleic acid
S: stearic acid The structured lipid synthesized enzymatically under the condition of 2% of lipozyme (w/w of total substrate) at 60° C. for 3 h was considered in this chapter for estimation of its calorific value (SL 3). A 1 kg scale preparation of this structured lipid was carried out for this purpose.

Almost all the products of normal lipid digestion and absorption appear in the lymph. Shortly after a fatty meal, there is a great increase in the level of lipids in the lymph. This elevated lipid burden of the lymph and hence the blood has been measured in several ways: as total lipid, as triacylglycerol constituting 90% of the lymph lipid and also as light-scattering particles (chylomicrons). Based on this principle, single oral dose experiment of the proposed structured lipid has been conducted on overnight fasting male Wistar rats. The absorption behavior of the structure lipid (SL 3) has been compared with that of sunflower oil (control) by estimating and comparing the plasma triacylglycerol level over a certain period of Lime (zero h, 1 h, 2 h and 3 h after oral dosing). In both the control and the experimental group, the peak value of plasma triacyiglycerol was found to be 2 h after loading of the fat. The level of plasma triacylglycerol was found to be significantly higher in the control group than the experimental group. The plasma as well as fecal total lipid fatty acid composition was also analyzed by gas-liquid chromatography to find the absorption pattern of individual fatty acids. No trace of behenic acid was observed in the plasma total lipid of the experimental group and total excretion of behenic acid was found in the experimental group. Amount of excreted lipid in the fecal material of the experimental group was found to be significantly higher than that of the control group. The encouraging result of this experiment has helped in designing the nutritional studies meant for calorific estimation.

A modified growth method was adopted for estimating the calorific value of the studied structured lipid taking sunflower oil as caloric control. The experiment was conducted on weanling NIN/Wistar male rats of initial body weights 65–70 g and age 28 days. AIN-93 G diet formulated for growth was considered as basal diet of all the test groups including the ad libitum group. Each test group along with ad libitum group contains seven numbers of rats. Basal feed consumption of the test groups is restricted to 50% of the feed consumed by the ad libitum group. Thus, all test groups receive equal amount of basal diet daily. These diets were modified by adding 5, 10 and 15% of sunflower oil for the control test groups, and 5 and 10% of studied structured lipid for the experimental test groups. Daily adjustment of the feed quantities helps in maintaining rapid growth. The experiment was conducted over 21 days. Body weights were recorded on 0, 3, 6, 9, 14, 17 and 21 days. To find the linear response of the body weight gain of the control animal against calorie intake, regression analysis was performed. Regression analysis was also performed to find the linear response of the body weight gain over 21 days of the conducted experiment. The calorific value of the structured lipid was determined by comparing the $21^{st}$ day mean growth of the rats fed with diets containing structured lipid to the $21^{st}$ day mean growth of the rats fed with diets containing varying levels of sunflower oil. After the cumulative weight gain was recorded for 21 days, regression analysis was performed with added calories from sunflower oil regressed against $21^{st}$ day body weight gains for the sunflower oil supplemented group. The slope and intercept calculated from the standard curve regression were used in the following formula, to estimate the calorific value of the structured lipid:

$$KCal_x = \frac{BWG_x - INT}{SLP \times K_x}$$

where $KCal_x$ is the estimated Kilocalories per gram of unknown oil i.e. the structured lipid in this assay. $BWG_x$ is the mean body weight gain on $21^{st}$ day for rats fed diets supplemented with 5% of structured lipid, INT is the intercept, SLP is the slope and $K_x$ is the amount of structured lipid added to the diet (grams per 100 g of the diet). An estimated value of 5.36 Kcal/g of the studied structured lipid was found against 9 Kcal/g provided by a natural oil or fat. After 21 days, blood as well as fecal samples were collected from all the groups for total lipid fatty acid composition analysis. The absorption pattern of individual fatty acids in this long term feeding experiment were identical to those observed in the single oral dose experiment. Two such growth studies were conducted.

Another growth study on ad libitum diet was also conducted on 21 days old weanling NIN/Wistar male rats having their initial body weights in the range of 39–40 g to find the metabolic behavior or the absorption pattern of the structured lipid. Twenty rats were divided into two groups. The AIN-93 G diet was taken as basal diet supplemented with 10% of sunflower oil for the control group and 10% of structured lipid for the experimental group. The experiment was conducted over 28 days and body weights were recorded on 0, 3, 5, 7, 14, 17, 19 and 21 days. The growth patterns of both the groups were found to be identical. Mean food intake of both the groups was also found to be identical in this ad libitum feeding experiment (9.8 g/day/rat for the control group and 9.9 g/day/rat for the experimental group. After 28 days of the experiment, blood sample as well as fecal samples were collected from both the groups for the total lipid fatty acid composition analysis. No significant difference in the level of major fatty acids were found between the two groups, though behenic acid was the predominant fatty acid excreted in the fecal material of the experimental group. All these result shows that the absorption pattern of this semisynthetic studied structured lipid is very similar to natural oil or fat.

The following are the main observations:
i. Incorporation of behenic acid into vegetable oil was achieved both by chemical interesterification and enzymatic transesterification.
ii. Structured lipid (SL 3), obtained by enzymatic transesterification between sunflower oil & ethyl behenate, provide 5.36 Kcal/g against 9 Kcal provided by native oil or fat.
iii. Lower caloric availability of SL 3 is because of the total excretion of behenic acid in the feces.
iv. Identical growth pattern and mean food intake of control and experimental group as found in growth study on ad libitum diet, confirms that the taste, palatability and absorption pattern of SL 3 is very similar to native oil or fat
v. The proposed structured lipid contain essential fatty acids and natural antioxidants and hence nutritionally better equipped than the reduced calorie structured lipids, available in the market.

found in HP 5 column was found to be in good agreement with the fatty acid compositions found in ST 2330 column.

TABLE 1

Amount of total lipid excreted in the fecal material in the first growth experimental on restricted diet

| Type of fecal fat | Test group | Mean ± SE (n = 3)* [mg/day] |
|---|---|---|
| Glycerol lipids | Control | 1.343 ± 0.54 |
|  | Experimental | 16.59 + 3.27[a] |
| Fatty Acid salts | Control | 7.82 ± 1.14 |
|  | Experimental | 52.72 ± 4.46[b] |

Figure 1A:
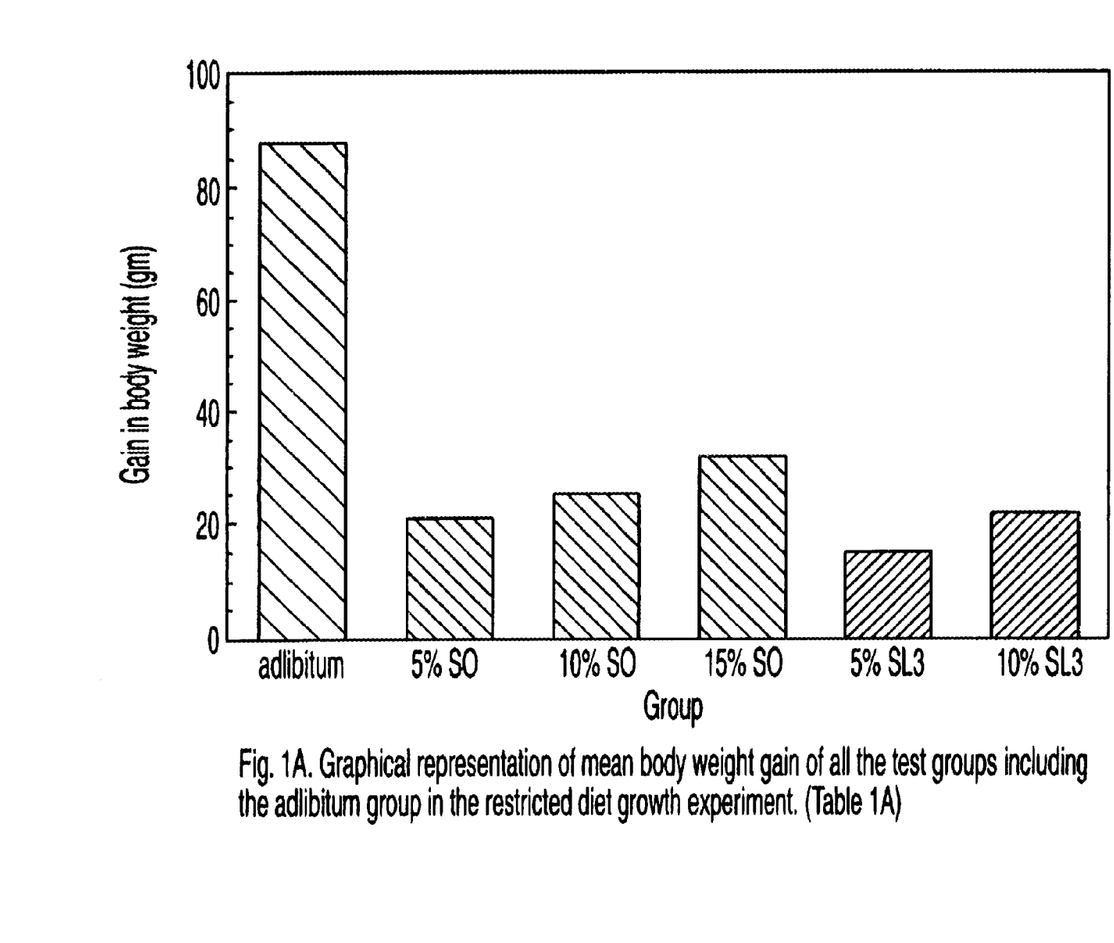
FIG. 1A is a graphical representation of mean body weight gain of all the test groups including the ad libitum group in the restricted diet growth experiment.
Figure 1B:
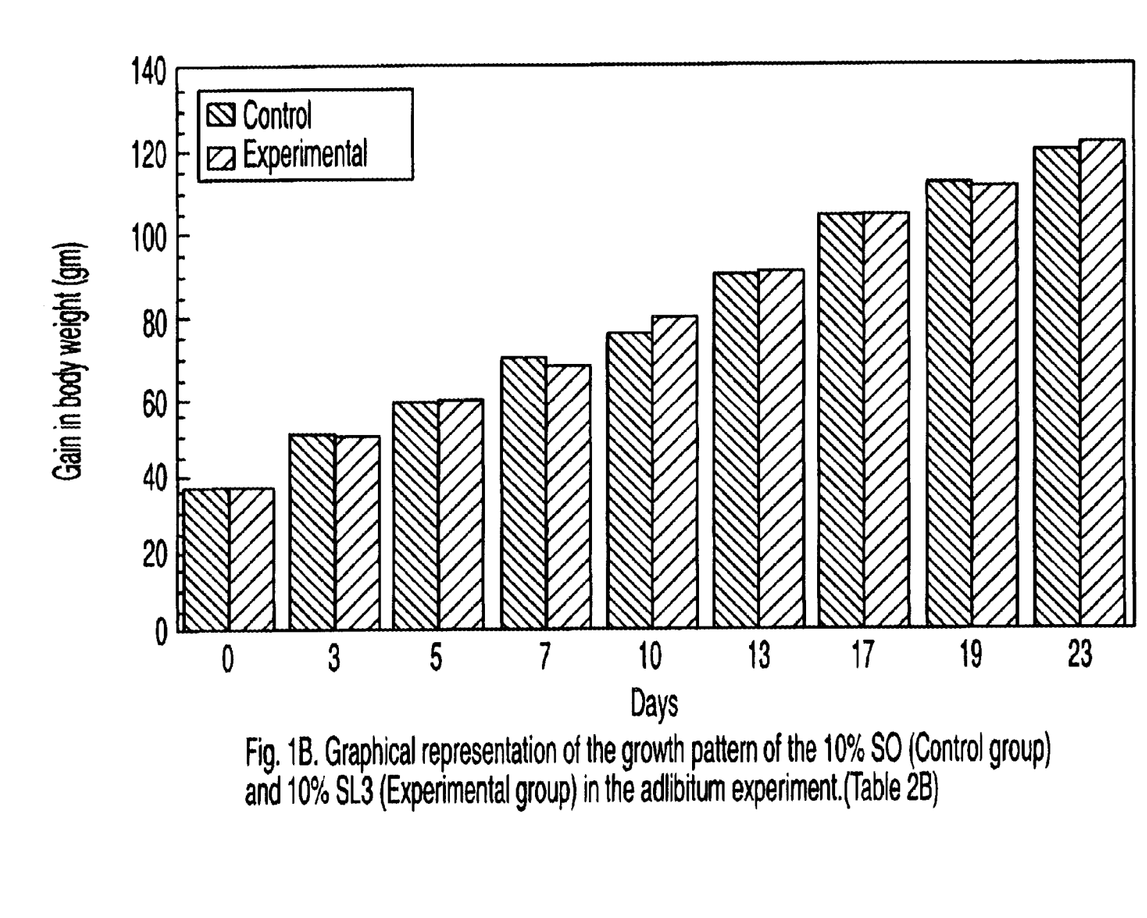

*n = Number of rats
[a-b]significantly different from control group: [a]$P < 0.02$, [b]$P < 0.001$ Growth study on restricted diet with 5% and 10% of structured lipid: Table 1A graphically illustrates the calories delivered by all the test groups. The two basic assumptions of this assay, that the weight gain of the rats is linearly related to kilo calories added to the diet and the weight gain is linear over 14 days of the experiment, are confirmed from Table 8. In Table 2, the mean cumulated weight gain of the five test groups on restricted diet were recorded for each of the time intervals when body weights were recorded over 21 days of the conducted experiment. Unlike Finley's assay (116), we have prolonged our experiment over 21 days. The slopes, intercepts and regression coefficients ($r^2$) are also reported in Table 2. When mean body weight gain was regressed against 21 days of assay for all the groups, regression coefficients were found to be greater than 0.987. This fulfills the first basic assumption of this assay. Similarly, mean body weight gain of the control groups fed varying levels of sunflower oil was also regressed against kilo calories added to the diet on each day when the body weights were recorded over 21 days of the conducted experiment. Linearity has been observed from the 9$^{th}$ day of the study regression analysis satisfying the other basic assumption of this assay. When 21$^{st}$ day mean body weight gain of all the control groups were regressed against kilo calories added to the diet, a regression coefficient of 0.993, intercept of 21.13 and slope of 0.2111 were obtained.

after 21 days of the conducted experiment. The fatty acid composition in the experimental group reflects dietary fatty acid intake, except that no trace of behenic acid was observed. For example, there is significantly higher level of C18.2, C18.3, C20.0 and C20.3 in the plasma lipid of 5% control group than the 5% experimental group, which is quite obvious. In 10% experiment, no such difference in the level of major fatty acid was observed between the two groups, control and experimental. This indicates that at 10% added fat level, the required levels of all major fatty acids were met in the experimental group. Even in 10% experimental group, no behenic acid was observed.

Three rats were chosen randomly from all the groups of 5% and 10% experiment for the fatty acid composition

TABLE 2

Mean body weight gains for various days and also against Kcal added to the diet.

| | Days of study regression analysis (±SE) | | | | | | | | |
|---|---|---|---|---|---|---|---|---|---|
| Groups | 0–3 | 0–6 | 0–9 | 0–14 | 0–17 | 0–21 | Intercept[a] | Slope[a,b] | [a]r² |
| 5% SO (353 Kcal) | −1.4 ± 0.085 | −0.78 ± 0.46 | 5.87 ± 0.67 | 9.75 ± 1.75 | 15 ± 1.75 | 21.5 ± 1.07 | −7.07 | 1.35 | 0.987 |
| 10% SO (378 Kcal) | −1.187 ± 0.37 | 2.12 ± 0.62 | 6.06 ± 0.79 | 11.87 ± 0.95 | 19.87 ± 1.18 | 25.68 ± 1.346 | −7.29 | 1.59 | 0.994 |
| 15% SO (403 Kcal) | 0.5 ± 0.834 | 4.68 ± 1.01 | 10.75 ± 1.157 | 16.62 ± 1.291 | 25.62 ± 1.451 | 32.05 ± 1.1498 | −6.02 | 1.859 | 0.997 |
| 5% SL3 | −2.629 ± 0.824 | −0.375 ± 0.632 | 3.81 ± 0.875 | 6.75 ± 0.963 | 11.94 ± 0.997 | 15.47 ± 1.801 | −6.28 | 1.068 | 0.997 |
| Intercept[c] | — | — | 5.12 | 9.312 | 14.8 | 21.13 | | | |
| Slope[c] | — | — | 0.098 | 0.1374 | 0.2124 | 0.2111 | | | |
| [c]r² | — | — | 0.780 | 0.976 | 0.998 | 0.993 | | | |

[a]Regression analyses of cumulative body weight gain at various times for each group
[b]grams of body weight gained/days of study
[c]Regression analysis of cumulative body weight gains against kilocalories added to the diet in the SO groups (control)

Estimation of calorific value of the structured lipid: As stated earlier, calorific availability of the structured lipid was determined by comparing the 21$^{st}$ day growth of the rats fed structured lipid to the 21$^{st}$ day growth of rats fed varying level of sunflower oil. After the cumulative weight gain was determined for 21 days, regression analyses were performed with added calories from sunflower oil regressed against 21$^{st}$ body weight gains for the sunflower oil supplemented groups. The slope and intercept calculated from the standard curve regression were used in the following formula to estimate the caloric value of the structured lipid. According to the formula, $$KCal_x = \frac{BWG_x - INT}{SLP \times K_x}$$

Where $Kcal_x$ is the estimated kilocalories per gram of the unknown oil i.e. the structured lipid in this assay, $BWG_x$ is the 21$^{st}$ day mean body weight gain for rats fed diets supplemented with 5% of structured lipid, INT is the intercept from the standard curve, SLP is the slope of the standard curve and $K_x$ is the amount of structured lipid added to the diet (grams per 100 g of the diet). Substituting all these values in the above equation, the estimated kilocalorie per gram of the structured lipid is found to be, $$Kcal/g = \frac{15.47 - 21.13}{0.2111 \times 5} = 5.36 \text{ Kcal/g}$$

Five rats were chosen randomly from each group for the fatty acid composition analysis of plasma total lipid contains the fatty acid composition in nanomoles per ml of plasma analysis of the fecal lipid. Extraction and analysis was performed separately as neutral lipid and also as soap.

A comparative presentation of the fatty acid composition of the excreted lipids, both as neutral lipid and as soap, are given between the control and experimental group in both 5% and 10% experiment. Data indicates that there was a significantly higher amount of excretion of all major fatty acids in the experimental group compared to the control group. An absolute excretion of behenic acid as neutral lipid and mostly as soap was also observed in the experimental group. No such excretion of behenic acid was found in the control group, which is a clear evidence of excreted behenic acid being a direct consequence of dietary intake. A comparative picture of the amount of excreted lipid between the control and experimental group in both the 5% and 10% experiment are shown below. Data depicts that there was a significantly higher amount of excretion of fecal lipid in the experimental group than the control group ($P<0.001$).

TABLE 2A

A comparative picture of the amount of excreted lipid (mg/day) in fecal material

| Type of experiment | Type of fecal lipid | Groups | Mean ± SE (n = 3)* |
|---|---|---|---|
| 5% Experiment | Neutral | Control | 0.866 ± 0.2 |
| | | Experimental | 17.83 ± 1.4[a] |
| | Soap | Control | 3.62 ± 0.4 |
| | | Experimental | 76.82 ± 7.6[a] |

TABLE 2A-continued

A comparative picture of the amount of excreted lipid (mg/day) in fecal material

| Type of experiment | Type of fecal lipid | Groups | Mean ± SE (n = 3)* |
|---|---|---|---|
| 10% Experiment | Neutral | Control | 1.93 ± 0.19 |
| | | Experimental | 7.38 ± 0.4[a] |
| | Soap | Control | 9.05 ± 0.8 |
| | | Experimental | 122.01 ± 7.9[a] |

*n = Number of rats
[a]Significantly different from control group $^a p < 0.001$ Growth study on ad libitum diet supplemented with 10% structural lipid: No difference was attributed between the two groups in their growth pattern over 21 days of the conducted experiment as is observed in Table 2B. This clearly depicts the similarity in the absorption behavior of structured lipid with the sunflower oil. Feed consumption of both the groups was recorded daily and here also no difference was observed between the two groups in their mean food intake. Mean food intake of the control group is 9.8 g/day/rat and that of experimental group is 9.9 g/day/rat.

This observation states that texture, flavor, and palatability of the structured lipid are very similar to natural oil.

All the rats from both the groups were chosen for the fatty acid composition analysis of plasma total lipid. In Table 3, the mean fatty acid composition of plasma total lipid in the control and the experimental group are given in wt %. There was no difference in the level of all fatty acids in the plasma between the two groups. This finding once again confirms the role played by the metabolic system in maintaining

TABLE 3

Analysis of fatty acid composition of plasma total lipid (in wt %) of the *ad libitum* experiment

| Fatty Acids | Fatty Acid (wt %) | |
|---|---|---|
| | Control* (n = 7) | Experimental* (n = 7) |
| 14:0 | 1.1 ± 0.1 | 1.2 ± 0.03 |
| 16:0 | 22.8 ± 0.4 | 21.7 ± 0.5 |
| 16:1 | 1.8 ± 0.4 | 2.7 ± 0.3 |
| 18:0 | 12.7 ± 0.6 | 12.3 ± 0.6 |
| 18:1 | 14.1 ± 0.3 | 12.9 ± 0.4 |
| 18:2 | 19.5 ± 0.9 | 19.5 ± 0.3 |
| 20:0 | 0.5 ± 0.1 | 0.7 ± 0.1 |
| 18:3 | 0.2 ± 0.07 | 0.3 ± 0.1 |
| 20:3 | 1.6 ± 0.4 | 2 ± 0.2 |
| 20:4 | 23.2 ± 0.9 | 24.7 ± 0.4 |
| 22:0 | — | — |
| 24:0 | 1.4 ± 0.2 | 0.8 ± 0.1 |
| 24:1 | 1.1 ± 0.1 | 1.2 ± 0.1 |

*Mean ± SE; n, number of rats the required level major fatty acids in the plasma. Three rats were chosen randomly from both the groups for their fecal lipid fatty acid composition analysis. Table 3 contains mean fatty acid composition of fecal lipid, neutral as well as soap, in both the control group and the experimental group.

TABLE 4

Analysis of fatty acid composition of fecal total lipid (in wt. %) in the *ad libitum* experiment (10% added fat)

| | Fatty Acid (wt %) | | | |
|---|---|---|---|---|
| | Neutral Lipid (n = 3)* | | Soap (n = 3)* | |
| Fatty Acids | Control | Experiment | Control | Experiment |
| 14:0 | 1.3 ± 0.3 | 0.5 ± 0.03 | 1.2 ± 0.2 | 0.1 ± 0.03 |
| 16:0 | 21 ± 0.5 | 11 ± 0.6[a] | 26.1 ± 1.3 | 7.2 ± 0.6[a] |
| 18:0 | 26 ± 2.5 | 10.4 ± 0.03[b] | 30.2 ± 2.1 | 9.3 ± 0.5[a] |
| 18:1 | 22 ± 0.3 | 9.8 ± 1.8[b] | 16.5 ± 1.9 | 1 ± 0.6[a] |
| 18:2 | 10.6 ± 3.2 | 3.8 ± 1.2 | 6.9 ± 0.2 | 0.3 ± 03[b] |
| 20:0 | 2.5 ± 0.2 | 3.9 ± 0.1 | 2.8 ± 0.3 | 4.1 ± 0.1[b] |
| 18:3 | 2.5 ± 0.2 | 1.2 ± 0.3 | 1.4 ± 0.8 | 0.1 ± 0.1[c] |
| 20:3 | 7.6 ± 1 | — | 9.5 ± 0.8 | — |
| 22:0 | — | 56.8 ± 3.6 | — | 75.6 ± 0.2 |
| 24:0 | 6.4 ± 0.2 | 2.6 ± 0.1[b] | 5.4 ± 0.3 | 2.3 ± 0.3[b] |

*Mean ± SE; n, number of rats
[a-b]Significantly different from control group $^a p < 0.001$, $^b p < 0.01$, $^c p < 0.02$ of excretion of palmitic and stearic acid in the control group than the experimental group, both as neutral lipid and soap. There was also an absolute excretion of behenic acid in the experimental group and the major excretion was as soap. There existed a significantly higher amount of excretion of fecal lipid as neutral lipid (P<0.01) and as soap (P<0.001) in the experimental group than the control group, as is observed in Table 5.

TABLE 5

Amount of excreted fecal lipid in the 10% SO (control group) and 10% SL3 (experimental) of the *ad libitum* experiment

| Types of fecal lipid | Types of test group | Amount of excreted lipid (mg/day), n = 3* |
|---|---|---|
| Neutral | Control | 2.9 ± 0.75 |
| | Experimental | 22.97 ± 4.36[a] |
| Soap | Control | 5.8 ± 2.1 |
| | Experimental | 134.7 ± 9.7[b] |

*Mean ± SE; n, number of rats
[a-b]Significantly different from control group $^a p < 0.01$, $^b p < 0.001$

Advantages of the Present Invention

1. The starting materials for the preparation of low calorie structured fat are the natural edible oils preferably vegetable oil sources like mustard, sunflower, safflower and groundnut (peanut) oils.
2. The process does nor involve any costly chemicals.
3. The reduced-calorie plastic fat prepared in the present invention has all the physical, chemical and biological attributes of a fat, consists only of triacylglycerols but deliver less calories and does not contain unnatural components such as very low molecular weight fatty acids.
4. The reduced-calorie fat contains essential fatty acids and natural antioxidants which are not present in the similar products reported earlier.
5. The reduced-calorie plastic fat does not contain any trans fatty acids which are usually present in the similar type of plastic fats prepared by partial hydrogenation.

What is claimed is:
1. A process for the preparation of a reduced calorie fat, which comprises:
   esterifying one or more edible oils with 1,3-dibehenin in the presence of a thermostable lipase enzyme, wherein the thermostable lipase enzyme is LIPOZYME, at a temperature in the range of about 25° C. to 150° C. for at least about 0.5 hr; and recovering the reduced calorie fat.

2. A process as claimed in claim 1 wherein the one or more edible oils used are selected from the group consisting of sunflower, safflower, groundnut, rapeseed, soybean, and fish oils.

3. A process as claimed in claim 1 wherein the esterification is effected in the time range of about 0.5 hr to 6 hr.

4. The process of claim 1, wherein the recovering comprises at least one of filtering the reduced-calorie fat and purifying the reduced-calorie fat.

5. The process of claim 4, wherein the purifying comprises at least one of washing and chromatographic separating.

6. The process of claim 5 wherein the chromatographic separating is accomplished using silic acid column chromotography.

7. The process of claim 1, wherein the thermostable lipase enzyme is present in an amount of about 0.3 to 0.5 weight percent.

8. The process of claim 1 wherein the reduced calorie fat recovered comprises palmitic acid, stearic acid, oleic acid, linoleic acid, arachidic acid, behenic acid, and lignoceric acid.

9. The process of claim 1, wherein the source of behenic acid is present in an amount from about 29.8 weight percent to 52.5 weight percent.

10. The process of claim 1, wherein the source of behenic acid is present in an amount from about 5 weight percent to 41 weight percent.

11. The process of claim 1, wherein the reduced calorie fat comprises linoleic acid in an amount from about 24.8 weight percent to 44.6 weight percent.

12. The process of claim 1, wherein the reduced calorie fat comprises linoleic acid in an amount from about 33 weight percent to 60 weight percent.

13. The process of claim 1, wherein the reduced calorie fat comprises:

palmitic acid present in an amount of about 4.9 weight percent;

stearic acid present in an amount of about 4.8 weight percent;

oleic acid present in an amount of about 17.1 weight percent;

linoleic acid present in an amount of about 35.2 weight percent;

arachidic acid present in an amount of about 1.7 weight percent;

behenic acid present in an amount of about 34.7 weight percent; and lignoceric acid present in an amount of about 1.6 weight percent.

* * * * *